US007482160B2

(12) United States Patent
Monahan et al.

(10) Patent No.: US 7,482,160 B2
(45) Date of Patent: *Jan. 27, 2009

(54) PROCESS OF MAKING A COMPOUND BY FORMING A POLYMER FROM A TEMPLATE DRUG

(75) Inventors: Sean D. Monahan, Madison, WI (US); David B. Rozema, Madison, WI (US); Vladimir Trubetskoy, Middleton, WI (US); Paul M. Slattum, Salt Lake City, UT (US); Jon A. Wolff, Madison, WI (US); Vladimir G. Budker, Middleton, WI (US); James E. Hagstrom, Middleton, WI (US); Lisa J. Hanson, Reno, NV (US)

(73) Assignee: Roche Madison Inc., Madison, WI (US)

( * ) Notice: Subject to any disclaimer, the term of this patent is extended or adjusted under 35 U.S.C. 154(b) by 317 days.

This patent is subject to a terminal disclaimer.

(21) Appl. No.: 11/322,419

(22) Filed: Dec. 30, 2005

(65) Prior Publication Data
US 2006/0159764 A1 Jul. 20, 2006

Related U.S. Application Data

(60) Continuation-in-part of application No. 10/004,763, filed on Dec. 5, 2001, now Pat. No. 7,049,144, and a continuation-in-part of application No. 09/312,351, filed on May 14, 1999, said application No. 10/004,763 is a division of application No. 09/464,871, filed on Dec. 16, 1999, now abandoned, which is a division of application No. 08/778,657, filed on Jan. 3, 1997, now Pat. No. 6,126,964, said application No. 09/312,351.

(60) Provisional application No. 60/085,764, filed on May 16, 1998, provisional application No. 60/009,593, filed on Jan. 4, 1996.

(51) Int. Cl.
*C12N 15/88* (2006.01)
(52) U.S. Cl. ...................... 435/458; 514/613
(58) Field of Classification Search ............... None
See application file for complete search history.

(56) References Cited

U.S. PATENT DOCUMENTS

| 4,861,719 | A | 8/1989 | Miller et al. |
| 5,149,543 | A | 9/1992 | Cohen et al. |
| 5,223,424 | A | 6/1993 | Cochran et al. |
| 5,264,618 | A | 11/1993 | Felgner et al. |
| 5,338,665 | A | 8/1994 | Schatz et al. |
| 5,585,481 | A | 12/1996 | Arnold et al. |
| 7,022,525 | B2 * | 4/2006 | Trubetskoy et al. ......... 435/455 |

FOREIGN PATENT DOCUMENTS

WO  WO9611712  4/1996

OTHER PUBLICATIONS

Anderson CF et al. "Salt-Nucleic Acid Interactions." Annu. Rev. Phys. Chem. 1995, vol. 46, pp. 657-700.

Arpicco S et al. "New Coupling Reagents for the Preparation of Disulfide Cross-Linked Conjugates with Increased Stability." Bioconjugate Chemistry 1997, vol. 8, pp. 327-337.

Arscott PG et al. "DNA Condensation by Cobalt Hexaammine (III) in Alcohol-Water Mixtures: Dielectric Constant and Other Solvent Effects." Biopolymers 1995, vol. 36, pp. 345-364.

Bloomfield VA "Condensation of DNA by Multivalent Cations: Considerations on Mechanism." Biopolymers 1991, vol. 31, pp. 1471-1481.

Boussif O et al. "A versatile vector for gene and oligonucleotide transfer into cells in culture and in vivo: polyethylenimine," Proc Natl Acad Sci USA 1995, vol. 92, pp. 7297-7301.

Bulaj G et al. "Ionization-Reactivity Relationships for Cysteine Thiols in Polypeptides." Biochemistry 1998, vol. 37, pp. 8905-8972.

Chattoraj DK et al. "DNA Condensation with Polyamines. II. Electron Microscopic Studies." J. Mol. Biol. 1978, vol. 121, pp. 327-337.

Chiou HC. et al. "Enhanced resistance to nuclease degradation of nucleic acids complexed to asialoglycoprotein-polylysine carriers." Nucleic Acids Research 1994, vol. 22, No. 24, pp. 5439-5446.

Danko I et al. "Pharmacological enhancement of in vivo foreign gene expression in muscle," Gene Ther. 1994, vol. 1, No. 2, pp. 114-121.

Darnell JE et al. 1986. "Molecular Cell Biology" New York: Scientific American Books, pp. 638-639, 642-643.

Felgner PL "Particulate systems and polymers for in vitro and in vivo delivery of polynucleotides." Advanced Drug Delivery Reviews 1990, vol. 5, pp. 163-187.

Fisher KJ et al. "Biochemical and functional analysis of an adenovirus-based ligand complex for gene transfer." Biochem J. 1994, vol. 299, pp. 49-58.

Fujimori K "Radical Polymerization of Methacrylic Acid in the Presence of Poly (4-vinylpyridine) in Methanol." Makromol. Chem. 1979, vol. 180, pp. 1743-1747.

Garcia-Ramirez M et al. "Condensation of DNA by basic proteins does not depend on protein composition." Biopolymers 1994, vol. 34, pp. 285-292.

Geuze HJ et al. "Immunocytochemical Localization of the Receptor for Asialoglycoprotein in Rat Liver Cells." J. Cell Biology 1982, vol. 92, pp. 865-870.

Golub El et al. "Transfection of DNA into adherent cells by DEAE-dextran/DMSO method increases drastically if the cells are removed from surface and treated in suspension." Nucleic Acids Research 1989, vol. 17, No. 12, pp. 4902.

(Continued)

*Primary Examiner*—James S Ketter
(74) *Attorney, Agent, or Firm*—Kirk Ekena; Mark K. Johnson

(57) ABSTRACT

A method of forming polymers in the presence of nucleic acid using template polymerization. These methods can be used for the delivery of nucleic acids, for condensing the nucleic acid, for forming nucleic acid binding polymers, for forming supramolecular complexes containing nucleic acid and polymer, and for forming an interpolyelectrolyte complex.

17 Claims, No Drawings

OTHER PUBLICATIONS

Gosule LC et al. "Compact form of DNA induced by sperimidine." Nature 1976, vol. 259, pp. 333-335.

Haynes M et al. "Structure of Nucleic Acid-Poly Base Complexes." Biochemistry 1970, vol. 9, No. 22, pp. 4410-4416.

Hsiang MW et al. "Structure of histone H1-DNA complex: Effect of histone H1 on DNA condensation." Biochemistry 1977, vol. 74, No. 11, pp. 4852-4856.

Hud NV. et al. "Identification Of The Elemental Packing Unit of DNA In Mammalian Sperm Cells By Atomic Force Microscopy." Biochemical and Biophysical Research Communications 1993, vol. 193, No. 3, pp. 1347-1354.

Kabanov AV et al. "DNA Complexes with Polycations for the Delivery of Genetic Material into Cells." Bioconjugate Chem. 1995, vol. 6, pp. 7-20.

Keire D et al. "Kinetics and Equilibria of Thiol/Disulfide Interchange Reactions of Selected Biological Thiols and Related Molecules with Oxidized Glutathione." J. Org. Chem. 1992, vol. 57, pp. 123-127.

Kishore K et al. "Polymers Containing disulfide, Tetrasulfide, Diselenide and Ditelluride Linkages in the Main Chain." Advances in Polymer Sciences 1995, vol. 121, pp. 83-117.

Kosturko LD et al. "Selective repression of transcription by base sequence specific synthetic polymers." Biochemistry 1979, vol. 18, pp. 5751-5756.

Lee R et al. "Folate-mediated Tumor Cell Targeting of Liposome-Entrapped Doxorubicin in Vitro." Biochimica et Biophysica Acta 1995, vol. 1233, pp. 134-144.

Leikin S et al. "Hydration Forces." Annu. Rev. Phys. Chem. 1993, vol. 44, pp. 369-395.

Lopata MA et al. "High level transient expression of a chloramphenicol acetyl transferase gene by DEAE-dextran mediated DNA transfection coupled with a dimethyl sulfoxide or glycerol shock treatment." Nucleic Acids Research 1984, vol. 12, No. 14, pp. 5707-5717.

Luthman H et al. "High efficiency polyoma DNA transfection of chloroquine treated cells." Nucleic Acids Research 1983, vol. 11, No. 5, pp. 1295-1308.

Marquet R et al. "Thermodyanamics of Cation-Induced DNA Condensation." Journal of Biomolecular Structure & Dynamics 1991, vol. 9, No. 1, pp. 159-167.

Martinek K et al. "Micellar Enzymology." Eur. J. Biochem. 1986, vol. 155, pp. 453-468.

Olmsted MC et al. "Grand Canonical Monte Carlo Molecular and Thermodynamic Predictions of Ion Effects on Binding of an Oligocation (L.sup.8+) to the Center of DNA Oligomers." Biophysical Journal 1995, vol. 68, pp. 634-647.

Perales JC et al. "An evaluation of receptor-mediated gene transfer using synthetic DNA-ligand complexes." Eur. J. Biochem. 1994, vol. 226, pp. 255-266.

Record MT Jr. et al. "Interpretation of Preferential Interaction Coefficients of Nonelectrolytes and of Electrolyte Ions in Terms of a Two-Domain Model." Biophysical Journal 1995, vol. 68, pp. 786-794.

Riemer SC et al. "Packaging of DNA in Bacteriophage Heads: Some Considerations on Energetics." Biopolymers 1978, vol. 17, pp. 785-794.

Sikorav J-L et al. "A Liquid Crystalline Phase in Spermidine-Condensed DNA." Biophysical Journal 1994, vol. 67, pp. 1387-1392.

Spolar RS et al. "Coupling of Local Folding to Site-Specific Binding of Proteins to DNA," Science 1994, vol. 263, pp. 777-784.

Stein VM et al. "Importance of Coulombic End Effects on Cation Accumulation Near Oligoelectrolyte B-DNA: A Demonstration using 23Na NMR." Biophysical Journal 1995, vol. 68, pp. 1063-1072.

Szajewski R et al. "Rate Constants and Equilibrium Constants for Thiol-Disulfide Interchange Reactions Involving Oxidized Glutathione." Journal of the American Chemical Society 1980, vol. 102, No. 6, pp. 2011-2025.

Thorpe P et al. "Comparison of Two Anti-Thy 1.1-Abrin A-Chain Immunotoxins Prepared With Different Cross-Linking Agents: Antitumor Effects, In Vivo Fate, and Tumor Cell Mutants." JNCI Nov. 1987, vol. 79 No. 5, pp. 1101-1112.

Trubetskoy VS, et al. "Quantitative assessment of DNA condensation." Anal Biochem 1999, vol. 267 No. 2, pp. 309-313.

van de Grampel HT et al. "Template Polymerization of N-Vinylimidazole alone Poly(methacrylic acid) in Water. 1. Influence of Template Concentration." Macromolecules 1990, vol. 23, pp. 5209-5216.

Wagner E et al. "Delivery of drugs, proteins and genes into cells using transferrin as a ligand for receptor-mediated endycytosis." Advanced Drug Delivery Reviews 1994, vol. 14, pp. 113-135.

Wagner E et al. "Influenza virus hemagglutinin HA-2 N-terminal fusogenic peptides augment gene transfer by transferrin-polylysine-DNA complexes: toward a synthetic virus-like gene-transfer vehicle." Proc Natl Acad Sci U S A. 1992, vol. 89 No. 17, pp. 7934-7938.

Widom J et al. "Cation-induced Toroidal Condensation of DNA. Studies with CO3+ (NH3)6" J. Mol. Biol. 1980, vol. 144, pp. 431-453.

Wilson RW et al. "Counterion-induces condensation of deoxyribonucleic acid. A light scattering study." Biochemistry 1979, vol. 18, No. 11, pp. 2192-2196.

Wolff J et al. "Direct Gene Transfer into Mouse Muscle in Vivo." Science Mar. 1990, vol. 247, pp. 1465-1468.

Zauner W et al. "Rhinovirus-Mediated Endosomal Release of Transfection Complexes." Journal of Virology, 1995, vol. 69, No. 2, pp. 1085-1092.

Zhang W etg al. "Large electrostatic differences in the binding thermodynamics of a cationic peptide to oligomeric and polymeric DNA." Biochemistry 1996, vol. 93, pp. 2511-2516.

* cited by examiner

PROCESS OF MAKING A COMPOUND BY FORMING A POLYMER FROM A TEMPLATE DRUG

CROSS-REFERENCE TO RELATED APPLICATIONS

This application is a continuation-in-part of application Ser. No. 10/004,763, filed Dec. 5, 2001, now U.S. Pat. No. 7,049,144 allowed, and a continuation-in-part of application Ser. No. 09/312,351, filed May 4, 1999, application Ser. No. 10/004,763 is a divisional of application Ser. No. 09/464,871, filed Dec. 16, 1999, now abandoned, which is a divisional of application Ser. No. 08/778,657, filed Jan. 3, 1997 now U.S. Pat. No. 6,126,964, which claims the benefit of U.S. Provisional Application No. 60/009,593, filed Jan. 4, 1996, and application Ser. No. 09/312,351 claims the benefit of U.S. Provisional Application No. 60/085,764, filed May 16, 1998.

BACKGROUND OF THE INVENTION

Bifunctional molecules, commonly referred to as crosslinkers, are used to connect two molecules together. Bifunctional molecules can contain homo or hetero-bifunctionality. The reversibility of disulfide bond formation makes them useful tools for the transient attachment of two molecules. Disulfides have been used to attach a bioactive compound and another compound (Thorpe 1987). Reduction of the disulfide bond releases the bioactive compound. Disulfide bonds may also be used in the formation of polymers (Kishore et al 1993).

There are many commercially available reagents for the linkage of two molecules by a disulfide bond. Additionally there are bifunctional reagents that have a disulfide bond present. Typically, these reagents are based on 3-mercaptopropionic acid, i.e. dithiobispropionate. However, the rate at which these bonds are broken under physiological conditions is slow. For example, the half life of a disulfide derived from dithiobispropionimidate, an analog of 3-mercaptopropionic acid, is 27 h in vivo (Arpicco et al. 1997). A stable disulfide bond is often desirable, for example when purification of linked molecules or long circulation in vivo is needed. For this reason, attempts have been made to make the disulfide less susceptible to cleavage.

It has been demonstrated that both stability, measured as reduction potential, and rate, measured as rate constants, of disulfide reduction are both related to the acidity of the thiols which constitute the disulfide. Additional factors that may affect the rate of reduction are steric interactions and intramolecular disulfide cleavage. Looking at the difference in the rates for the reactions RSH+R'SSR'→RSSR'+R'SH and RSH+R"SSR"→RSSR"+R"SH, it has been demonstrated that $\log k''/k' = \beta(pK_a^{R'} - pK_a^{R''})$, where k' and k" are the rate constant for the reactions with R'SSR' and R"SSR" respectively, $pK_a^{R'}$ and $pK_a^{R''}$ are the acidities of the thiol groups R'SH and R"SH, and β is a constant determined empirically to be 0.72. From this equation, one would predict that the reduction of a disulfide composed from relatively acidic thiols would be reduced more quickly than one composed of less acidic thiols. In support of this observation, it has been demonstrated that the disulfides cystine ($pK_a$ 8.3) and cystamine ($pK_a$ 8.2) are reduced 3-15 times faster than oxidized glutathione ($pK_a$ 8.9) (Bulaj et al. 1998).

It has been demonstrated that both stability (thermodynamics), measured as reduction potential (Keire 1992), and rate (kinetics), measured as rate constants, of disulfide reduction are both related to the acidity of the thiols which constitute the disulfide (Szajewski et al. 1980). The increase in acidity of a thiol is dependent upon one or more of the following structural factors: the presence of electron withdrawing groups which stabilize the thiolate through sigma and pi bonds (inductive effect), the presence of electron withdrawing groups that stabilize the thiolate through space or solvent (field effects), pi bonds which allow the negative charge to be placed on other atoms (resonance stabilization), and hydrogen bond donating groups within the molecule that can interact internally with the thiolate. For example, cysteine has an amino group two atoms from the thiol, which is more electron withdrawing than the amide nitrogen that is two atoms from the thiol in glutathione. As a consequence of this difference in electron withdrawing groups, the thiol of cysteine is 0.6 pK units more acidic than glutathione, and as mentioned previously, cystine is reduced 3-15 times faster than oxidized glutathione. Another example of a relatively acidic thiol is 5-thio-2-nitrobenzoic acid, $pK_a$ 5. Its acidity is due to resonance stabilization and inductive effects. Its disulfide is rapidly reduced by all standard alkyl thiols and its colored thiolate makes it a convenient assay for thiol concentration.

SUMMARY OF THE INVENTION

In a preferred embodiment a process is described for the delivery of a compound to a cell comprising: associating molecules with the compound, such as a polyion, modifying the molecules with an disulfide bond containing crosslinking reagent to form a complex, and contacting the cell with the complex. The compound may comprise polynucleotides, proteins or synthetic polymers. A preferred disulfide bond containing crosslinking reagent consists of an activated disulfide crosslinking reagent. The activated disulfide crosslinking reagent comprises an activated disulfide bond located between at least two reactive groups.

In a preferred embodiment a composition is described for delivering a polynucleotide to a cell comprising: a polynucleotide/polymer complex stabilized by an activated disulfide bonding-containing crosslinking. A preferred polynucleotide/polymer complex is a non-viral complex. The complex is formed by associating one or more polymers with the polynucleotide, and crosslinking the polymer(s) or the polymer(s) and the polynucleotide using an activated disulfide crosslinking reagent. Associating a polymer with a polynucleotide may condense the polynucleotide. Crosslinking, or stabilizing, the complex results in the complex being more resistant to aggregation or disassociation when exposed to conditions such as increased salt concentration or polyion presence.

DETAILED DESCRIPTION

A process for drug delivery is described in which polymerization and chemical reaction processes take place in the presence of the drug, such as a nucleic acid, in order to deliver the drug. Previously, the occurrence of chemical reactions or the process of polymerization in the presence of the nucleic acid has been avoided when delivering nucleic acid. We show that polymerization can be performed in the presence of nucleic acids without causing loss of function or activity of the nucleic acid. By having chemical reactions take place in the presence of the drug, also called a template polymer, small stable complexes can be formed. The process can be used to form polymers in the presence of the template polymer, to crosslink components an interpolyelectrolyte complex thereby stabilizing the complex, or to add functional groups to a polymer/template polymer complex.

An advantage of this described process of template polymerization is that polymers can be formed in association with nucleic acid that would otherwise be unable to become associated with the nucleic acid if the polymer was formed first. For example, the polymerization process can result in a hydrophobic polymer that is not soluble in aqueous solutions unless it is associated with nucleic acid. It is also possible to cross-link polymers in the presence of a polyion, thereby forming a more stable complex of polymer and nucleic acid. The crosslinked complex can become too stable such that the nucleic acid is unable to be dissociated and expressed when delivered to a cell. By incorporating labile bonds into either the polymers, crosslinking agents, or both, it is possible to make small stable nucleic acid-containing complexes that are able to release the nucleic acid upon delivery of the complex to a cell.

Activated disulfide crosslinking reagents contain a disulfide bond that is cleaved at a faster rate than glutathione (when measured under the same conditions) and heterobifunctional or homobifunctional reactive groups located on either side of the labile disulfide bond. Such a compound can be described as a disulfide bond-containing bifunctional molecule: A-S-S-A'. More particularly, the crosslinking reagent contains a disulfide bond with one or more electronegative groups (electron withdrawing groups) within proximity of the disulfide bond which serve to lower the $pK_a$ of the constituent thiols. The reactive groups enable the crosslinker to form covalent linkages to another molecule or molecules without breaking the disulfide bond of the crosslinker. Reactive groups are selected to react with functional groups of the polymer. Reactive groups are selected to not react or to react minimally with the polynucleotide (or compound to be delivered). Exemplary activated disulfide crosslinking reagents may contain an aliphatic (I) or aromatic (II) disulfide bond, a disulfide bond that is connected directly to an aromatic or aliphatic heterocyclic ring (III), a disulfide bond that is connected directly to a ring system (aromatic or non-aromatic) through one of the sulfur atoms and to an aliphatic carbon through the other sulfur atom (IV), a disulfide bond that is connected directly to a heterocyclic ring system through one of the sulfur atoms and to a aliphatic carbon through the other sulfur atom (V) or a disulfide bond that is connected directly to a heterocyclic ring system (aromatic or non-aromatic) through one of the sulfur atoms and to an aromatic ring system through the other sulfur atom (VI). The heterocyclic ring may contain 5 or more atoms of which 1 or more is a heteroatom (X; sulfur, oxygen, nitrogen, or phosphorus), and the rest being carbon atoms.

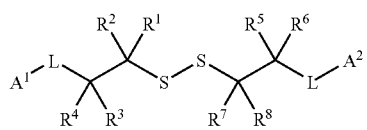

activated disulfide crosslinking reagent I

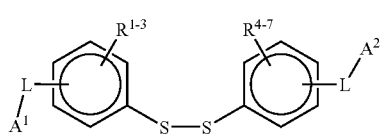

activated disulfide crosslinking reagent II

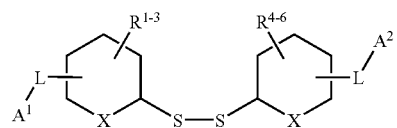

activated disulfide crosslinking reagent III

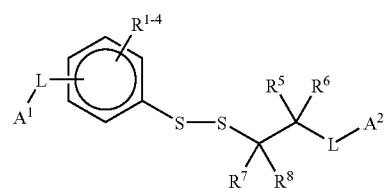

activated disulfide crosslinking reagent IV

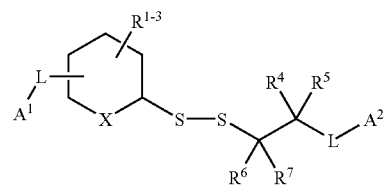

activated disulfide crosslinking reagent V

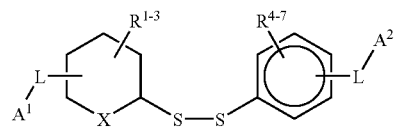

activated disulfide crosslinking reagent VI

The substituents, $R^1$-$R^{13}$, are selected such that the $pK_a$ of at least one of the constituent thiols is decreased. At least one of $R^1$-$R^{13}$ is an electronegative atom or functionality and may be selected from the group comprising: OH, OR (an ether), $NH_2$, (also secondary, tertiary, and quaternary amines), $SO_3^-$, COOH, COOR (an ester), $CONH_2$, $CONR_2$ (substituted amide), a halogen (F, Cl, Br, I), $NO_2$, H(IV), and $CH_3$ (or longer branched or straight chain, saturated, or unsaturated aliphatic group (II, III and IV). The substitution pattern on the aromatic ring may be varied to alter the reduction potential of the disulfide bond (II, III, VI). L is defined as a linker or spacer group that provides a connection between the disulfide and the reactive heterobifunctional or homobifunctional groups, $A^1$ and $A^2$. L may or may not be present and may be chosen from a group that includes alkanes, alkenes, alkynes (I, V, VI), esters, ethers, glycerol, amide, urea (I, V, VI), saccharides, polysaccharides, heteroatoms such as oxygen, sulfur, or nitrogen. The spacer may be charge positive, charge negative, charge neutral, or zwitterionic. $A^1$ and $A^2$ are selectively reactive functional groups and may be identical as in a homobifunctional molecule, or different as in a heterobifunctional molecule. In a preferred embodiment, the disulfide compounds contain selectively reactive functional groups that can undergo acylation or alkylation reactions. Selectively reactive functional groups are capable of forming new covalent bonds without affecting other groups in the molecule. Selectively reactive functional groups include (but are not limited to) isothiocynanate, isocynanate, acyl azide, acid halide (I, V, VI), O-acyl urea (I, V, VI), N-hydroxysuccinimide esters, succinimide esters, amide (I, V, VI), urea (I, V, VI), sulfonyl chloride, aldehyde, ketone (I, V, VI), ether (I, V, VI), epoxide, carbonate, alkyl halide (I, V, VI), imidoester, carboxylate, alkylphosphate, arylhalides (e.g. difluoro-dinitrobenzene) anhydrides (I, V, VI), or succinic anhydride (II, III, IV).

For Example:

If functional group $A^1$, $A^2$ is an amine then $A^1$, $A^2$ can react with (but not restricted to) an activated carboxylic acid, isothiocyanate, isocyanate, acyl azide, alkyl halide, acid halide, N-hydroxysuccinimide ester, sulfonyl chloride, aldehyde, ketone, epoxide, carbonate, imidoester, amide, carboxylate, or alkylphosphate, arylhalides (difluoro-dinitrobenzene) or anhydrides. In other terms when function $A^1$, $A^2$ is an amine, then an acylating or alkylating agent can react with the amine.

If functional group $A^1$, $A^2$ is a sulfhydryl then $A^1$, $A^2$ can react with (but not restricted to) a haloacetyl derivative, activated carboxylic acid, maleimide, aziridine derivative, acryloyl derivative, or fluorobenzene derivatives.

If functional group $A^1$, $A^2$ is carboxylate then $A^1$, $A^2$ can react with (but not restricted to) a diazoacetate, alcohol, thiol or an amine once the acid has been activated.

If functional group $A^1$, $A^2$ is an hydroxyl then $A^1$, $A^2$ can react with (but not restricted to) an activated carboxylic acid, epoxide, oxirane, or an amine in which carbonyldiimidazole is used.

If functional group $A^1$, $A^2$ is an aldehyde or ketone then $A^1$, $A^2$ can react with (but not restricted to) an hydrazine, hydrazide derivative, amine (to form a Schiff Base that may or may not be subsequently reduced by reducing agents such as $NaCNBH_3$), or a diol to form an acetal or ketal.

If functional group $A^1$, $A^2$ is an activated carboxylic acid, isothiocyanate, isocyanate, acyl azide, N-hydroxysuccinimide ester, sulfonyl chloride, aldehyde, ketone, epoxide, carbonate, imidoester, alkylphosphate, arylhalides (difluoro-dinitrobenzene), anhydride, alkyl halide, or acid halide, p-nitrophenyl ester, o-nitrophenyl ester, pentachlorophenyl ester, pentafluorophenyl ester, carbonyl imidazole, carbonyl pyridinium, or carbonyl dimethylaminopyridinium, then $A^1$, $A^2$ can react with (but not restricted to) an amine, a hydroxyl, hydrazine, hydrazide, or sulfhydryl group.

If functional group $A^1$, $A^2$ is an aldehyde, ketone, epoxide, oxirane, or an amine in which carbonyldiimidazole or N,N'-disuccinimidyl carbonate is used, then $A^1$, $A^2$ can react with (but not restricted to) a hydroxyl.

If functional group $A^1$, $A^2$ is a hydrazine, hydrazide derivative, or amine (primary or secondary) then $A^1$, $A^2$ can react with (but not restricted to) an aldehyde or ketone (to form a Schiff Base that may or may not be reduced by reducing agents such as $NaCNBH_3$).

Counterintuitive to previous efforts to synthesize bifunctional molecules with stabile disulfides, the object of the current invention is to synthesize labile disulfide molecules. In vivo, disulfides are primarily reduced by the cysteine-based thiol glutathione (γ-glutamylcystylglycine), which is present in millimolar concentrations in the cell. To increase the lability of the disulfide bond in a bifunctional molecule and its construct, we have synthesized several disulfide bond-containing bifunctional molecules that are more rapidly reduced than oxidized glutathione.

Disulfide Bond Containing Bifunctional Molecules:

Bifunctional molecules, possessing either homo or heterobifunctionality (commonly referred to as crosslinkers), are used to connect two molecules together. The disulfide linkage (RSSR') may be used within bifunctional molecules. The reversibility of disulfide bond formation makes them useful tools for the transient attachment of two molecules. Physiologically, disulfides are reduced by glutathione.

A disulfide bond that is labile under physiological conditions means: the disulfide bond is cleaved more rapidly than oxidized glutathione or any disulfide constructed from thiols in which one of the constituent thiols is more acidic, lower pKa, than glutathione or is activated by intramolecular attack by a free thiol. Constituent in this case means the thiols that are bonded together in the disulfide bond. Cleavable means that a chemical bond between atoms is broken.

The present invention describes physiologically labile disulfide bond containing bifunctional molecules. The present invention is also meant to include constructs prepared from the bifunctional molecules, including polymers, peptides, proteins, nucleic acids, polymer nucleic acid complexes. Construct means any compound resulting from the chemical reaction of at least one of the reactive centers of the bifunctional molecule resulting in new chemical bond other that that resulting from hydrolysis of both reactive centers of the bifunctional molecule. Further chemical modification may occur after the formation of the construct. Crosslinking refers to the chemical attachment of two or more molecules with a bifunctional reagent. A bifunctional reagent is a molecule with two reactive ends. The reactive ends can be identical as in a homobifunctional molecule, or different as in a heterobifunctional molecule.

Polymers:

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

To those skilled in the art of polymerization, there are several categories of polymerization processes that can be utilized in the described process. The polymerization can be chain or step (M. P. Stevens Polymer Chemistry: An Introduction New York Oxford University Press 1990). Template polymerization is the formation of polymers using pre-existing polymers and/or complexes of pre-existing polymers. In this way, template polymerization is used to form polymers from daughter polymers.

Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields -[A-B]-Or the other approach is to have two bifunctional monomers. A-A+B-B yields -[A-A-B-B]-Generally, these reactions can involve acylation or alkylation. Acylation is defined as the introduction of an acyl group (—COR) onto a molecule. Alkylation is defined as the introduction of an alkyl group onto a molecule. If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate activated with a carbodiimide, alkylphosphate, arylhalides (difluoro-dinitrobenzene), anhydride, or acid halide, p-nitrophenyl ester, o-nitrophenyl ester, pentachlorophenyl ester, pentafluorophenyl ester, carbonyl imidazole, carbonyl pyridinium, or carbonyl dimethylaminopyridinium. In other terms when function A is an amine then function B can be acylating or alkylating agent or amination agent.

If functional group A is a sulfhydryl then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which a carbodiimide is used. Other additives may be utilized such as carbonyldiimidazole, dimethylamino pyridine (DMAP), N-hydroxysuccinimide or alcohol using carbodiimide and DMAP.

If functional group A is an hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used. If functional group A is an aldehyde or ketone then function B can be (but not restricted to) an hydrazine, hydrazide derivative, amine (to form a Schiff Base that may or may not be reduced by reducing agents such as NaCNBH3) or hydroxyl compound to form a ketal or acetal.

Yet another approach is to have one bifunctional monomer so that A-A plus another agent yields -[A-A]-.

If function A is a sulfhydryl group then it can be converted to disulfide bonds by oxidizing agents such as iodine ($I_2$) or $NaIO_4$ (sodium periodate), or oxygen ($O_2$). Function A can also be an amine that is converted to a sulfhydryl group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azide (including halogenated aryl azide), diazo, benzophenone, alkyne or diazirine derivative.

Reactions of the amine, hydroxyl, sulfhydryl, carboxylate groups yield chemical bonds that are described as amide, amidine, disulfide, ethers, esters, enamine, imine, urea, isothiourea, isourea, sulfonamide, carbamate, alkylamine bond (secondary amine), carbon-nitrogen single bonds in which the carbon contains a hydroxyl group, thioether, diol, hydrazone, diazo, or sulfone.

Monomers containing (but not limited to) vinyl, acrylate, methacrylate, acrylamide, methacrylamide groups can undergo chain reaction which can be radical, anionic, or cationic. Chain polymerization can also be accomplished by cycle or ring opening polymerization. Several different types of free radical initiators could be used that include peroxides, hydroxy peroxides, and azo compounds such as 2,2'-Azobis (-amidinopropane) dihydrochloride (AAP).

Crosslinking of DNA-Polymer Post Complexes:

It has been shown that covalent crosslinking of polyamines in complexes with DNA increases the stability of the condensed DNA particles in salt (Trubetskoy et al. *Bioconjugate Chemistry* 1999). This process, termed caging, is a form of template polymerization in that new, larger polymers are formed as the crosslinking reagent forms new polymer bonds between the polyamines. In this way, disulfide-containing polymers may then be constructed by caging condensed DNA complexes with disulfide-containing crosslinking reagents. The disulfide crosslinkers may also crosslink (i.e. template polymerize) other molecules that are in association with a compound of interest. A complex is stabilized by crosslinking (or caging) if the crosslinking causes the complex to be more resistant to aggregation or disassembly in the presence of physiological levels of salt or serum.

Types of Monomers:

A wide variety of monomers can be used in the polymerization processes. These include positive charged organic monomers such as amine salts, imidine, guanidine, imine, hydroxylamine, hydrozyine, heterocycle (salts) like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Other Components of the Monomers and Polymers:

The polymers can have functional groups that increase their utility. Functional groups can be present on the monomers prior to association with the template polymer, they may be incorporated into the polymer during an initial template polymerization stage or they may be incorporated during a subsequent polymerization step. Functional groups can enhance targeting of the polymer or complex to a cell type or subcellular location, enhance membrane permeability. Functional groups include: targeting groups, reporter or marker molecules, spacers, steric stabilizers, chelators, polycations, polyanions, and polymers.

Cross-linking is the linking of two moieties of one or more polymers to one another using a bifunctional, or multifunctional, chemical linker. One result is that the polymer, as a network, becomes stronger and more resistant to being dissolved. Covalent linking bifunctional linkers may be homobifunctional (which involves the same chemical reaction for linking both moieties) or heterobifunctional (involves two different reactions allowing linkage of different functional groups). By cross-linking, a cage may be formed around or near the polyion creating a complex of polyion and polymer.

A cross-linker may be chosen such that cross-linking a polycation-polynucleotide complex reduces the net charge of the complex. The net charge of a polycation-polynucleotide complex may also be reduce by modifying charged moieties on the polycations after the complex has been stabilized by crosslinking. Functional groups such a targeting groups and steric stabilizers may be used to reduce or shield the charge of a complex.

Targeting groups are used for targeting the polymer-nucleic acid complexes to specific cells or tissues. Examples of targeting groups include molecules (ligands) that enhance binding to cell receptors, such as the asialoglycoprotein receptor by using asialoglycoproteins or galactose residues. Proteins such as insulin, EGF, or transferrin can be used for targeting. Peptides that include the RGD sequence can be used to target many cells. Polypeptide includes proteins and peptides, modified proteins and peptides, and non-natural proteins and peptides. Binding of ligands to receptors often initiates endocytosis. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

Other targeting groups can be used to increase the delivery of the drug or nucleic acid to certain parts of the cell. For example, agents can be used to disrupt endosomes and a nuclear localizing signal (NLS) can be used to target the nucleus. The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines, acyl hydrazones, and Schiff bases.

Functional groups that enhance release from intracellular compartments (releasing signals) can enhance release from intracellular vesicles such as endosomes and lysosomes. Release includes movement out of an intracellular compartment into cytoplasm. Such groups include, but are not limited to: viral components such as influenza virus hemagglutinin subunit HA-2 peptides and other types of amphipathic peptides.

Reporter or marker molecules are compounds that can be easily detected. Typically they are fluorescent compounds such as fluorescein, rhodamine, Texas red, CY®5, CY®3 or dansyl compounds. They can be molecules that can be detected by UV or visible spectroscopy or by antibody interactions or by electron spin resonance. Biotin is another reporter molecule that can be detected by labeled avidin. Biotin could also be used to attach targeting groups.

A spacer is any linker known to those skilled in the art to enable one to join one moiety to another moiety. The moieties can be hydrophilic or hydrophobic. Preferred spacer groups include, but are not limited to C1-C12 alkyl, C1-C12 alkenyl, C1-C12 alkynyl, C6-C18 aralkyl, C6-C18 aralkenyl, C6-C18 aralkynyl, ester, ether, ketone, alcohol, polyol, amide, amine, polyglycol, polyamine, thiol, thio ether, thioester, phosphorous containing, and heterocyclic.

Another functional group comprises compounds, such as polyethylene glycol, that decrease interactions between molecules and themselves and with other molecules. Such groups are useful in limiting interactions such as between serum factors or cells and the molecule or complex to be delivered. These groups are referred to as steric stabilizers or interaction modifiers. A steric stabilizer can be a long chain hydrophilic group that prevents aggregation by sterically hindering particle to particle electrostatic interactions. Examples include: alkyl groups, PEG chains, poloxamers, polysaccharides, hydrogen molecules, alkyl amines. An interaction modifier changes the way that a molecule interacts with itself or other molecules, relative to a molecule containing no interaction modifier. For example, polyethylene glycol is an interaction modifier that decreases interactions between molecules and themselves and with other molecules.

Another functional group comprises alkyl chains and other hydrophobic groups such as cholesterol and cholesterol derivatives. These hydrophobic groups can be used to bind to membranes, disrupt membranes, or provide hydrophobic interactions.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule.

Salts are ionic compounds that dissociate into cations and anions when dissolved in solution. Salts increase the ionic strength of a solution, and consequently decrease interactions between nucleic acids with other cations.

The present invention provides for the transfer of polynucleotides, and biologically active compounds into parenchymal cells within tissues in situ and in vivo, utilizing disulfide bonds that can be cleaved under physiological conditions, and delivered intravasculary (U.S. patent application Ser. No. 08/571,536), intrarterially, intravenous, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thyroid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands.

Delivered means that the polynucleotide becomes associated with the cell. The polynucleotide can be on the membrane of the cell or inside the cytoplasm, nucleus, or other organelle of the cell. The process of delivering a polynucleotide to a cell has been commonly termed transfection or the process of transfecting and also it has been termed transformation. The polynucleotide could be used to produce a change in a cell that can be therapeutic. The delivery of polynucleotides or genetic material for therapeutic and research purposes is commonly called gene therapy. The polynucleotides or genetic material being delivered are generally mixed with transfection reagents prior to delivery.

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, hormones, cytokines, antigens, viruses, oligonucleotides, and nucleic acids are examples of biologically active compounds. Bioactive compounds may be used interchangeably with biologically active compound for purposes of this application.

The term nucleic acid is a term of art that refers to a polymer containing at least two nucleotides. Nucleotides contain a sugar deoxyribose (DNA) or ribose (RNA), a base, and a phosphate group. Nucleotides are linked together through the phosphate groups. Bases include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. The term nuclei acid includes deoxyribonucleic acid (DNA) and ribonucleic acid (RNA). DNA may be in the form of anti-sense, plasmid DNA, parts of a plasmid DNA, vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups. Anti-sense is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothionates, and other variants of the phosphate backbone of native nucleic acids. In addition, DNA and RNA may be single, double, triple, or quadruple stranded. Expression cassette refers to a natural or recombinantly produced polynucleotide molecule which is capable of expressing protein(s). A DNA expression cassette typically includes a promoter (allowing transcription initiation), and a sequence encoding one or more proteins. Optionally, the expression cassette may include trancriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

The term naked polynucleotides indicates that the polynucleotides are not associated with a transfection reagent or other delivery vehicle that is required for the polynucleotide to be delivered to the cardiac muscle cell. A transfection reagent or delivery vehicle is a compound or compounds used in the prior art that bind(s) to or complex(es) with oligonucleotides or polynucleotides, and mediates their entry into cells.

Condensed Nucleic Acids: Condensing, or compacting, a polymer, such as nucleic acid, means decreasing the effective volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism. The size of DNA/polymer complex is important for gene delivery in vivo.

A significant number of multivalent cations with widely different molecular structures have been shown to induce the condensation of polynucleotides. These include spermidine, spermine, $Co(NH_3)_6^{3+}$, protamine, histone H1, and polylysine (Gosule L C et al. 1976, Chattoraj D K et al. 1978, Had N V et al. 1993, Hsiang M W et al. 1977, Haynes M et al. 1970, Widom J et al. 1980). Quantitative analysis has shown DNA condensation to be favored when 90% or more of the charges along the sugar-phosphate backbone are neutralized (Wilson R W et al. 1979).

Intravascular: An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

Electron withdrawing group is any chemical group or atom composed of electronegative atom(s), that is atoms that tend to attract electrons. Resonance stabilization is the ability to distribute charge on multiple atoms through pi bonds. The inductive effective, in a molecule, is a shift of electron density due to the polarization of a bond by a nearby electronegative or electropositive atom.

An activated carboxylate is a carboxylic acid derivative that reacts with nucleophiles to form a new covalent bond. Nucleophiles include nitrogen, oxygen and sulfur-containing compounds to produce ureas, amides, carbonates, esters, and thioesters. The carboxylic acid may be activated by various agents including carbodiimides, carbonates, phosphoniums, uroniums to produce activated carboxylates acyl ureas, acylphosphonates, and carbonates. Activation of carboxylic acid may be used in conjunction with hydroxy and amine-containing compounds to produce activated carboxylates N-hydroxysuccinimide esters, hydroxybenzotriazole esters, N-hydroxy-5-norbornene-endo-2,3-dicarboximide esters, p-nitrophenyl esters, pentafluorophenyl esters, 4-dimethylaminopyridinium amides, and acyl imidazoles.

U.S. application Ser. No. 10/004,763 is incorporated herein by reference.

EXAMPLES

Example 1

Synthesis of Disulfide-Containing Crosslinking Dialdehyde

Thiol-containing diol 1-thioglycerol was oxidized to the disulfide by addition of an excess of iodine in methylene chloride, and the excess iodine was reduced by the addition of sodium thiosulfate. The resulting disulfide was then purified by reverse phase HPLC. Oxidation of the vicinal diol was accomplished by the addition of >5 molar equivalents of sodium periodate in water. The oxidation was allowed to proceed for 3 h before crosslinking.

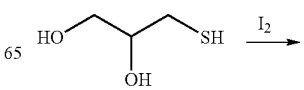

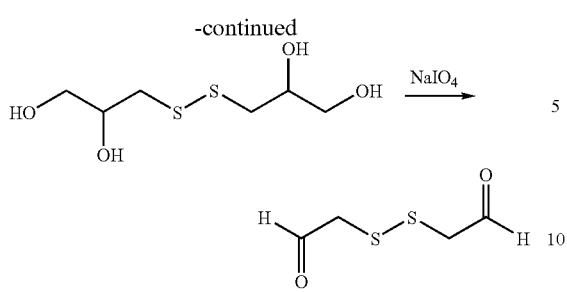

Example 2

Synthesis of Polyvinylethers

2-Vinyloxy Ethyl Phthalimide was synthesized according to literature procedure from phthalimide and 2-chloroethyl vinyl ether. 2-chloroethyl vinyl ether, phthalimide, ethyl vinylether, propyl vinyl ether, butyl vinyl ether, and boron trifluoride diethyl etherate ($BF_3 \cdot OEt_2$) were purchased from Aldrich. Methyl vinyl ether was purchased from Matheson. Melittin was synthesized by an Applied Biosystems 433A peptide synthesizer using standard peptide synthesis methods.

2-Vinyloxy Ethyl Phthalimide (1 g, 4.6 mmol) and methyl vinylether (0.267 g, 4.6 mmol), ethyl vinylether (0.332 g, 4.6 mmol), propyl vinylether (0.396 g, 4.6 mmol) or butyl vinylether (0.460 g, 4.6 mmol) were dissolved in 25 mL anhydrous dichloromethane. These solutions were then brought to −78° C., $BF_3 \cdot OEt_2$ (0.065 g, 0.46 mmol) was added and the reaction was allowed to proceed for 3 h at −78° C. The polymerization was then stopped by the addition of 50/50 mixture of ammonium hydroxide in methanol. The solvents were then removed by rotary evaporation. The polymer was dissolved in 30 mL of 1,4-dioxane/methanol (2/1). To this solution was added hydrazine (0.147 g, 46 mmol) and the mixture was heated to reflux for 3 h. The solvents were then removed by rotary evaporation and the resulting solid was brought up in 20 mL of 0.5M HCl, refluxed for 15 min, diluted with 20 mL distilled water, and refluxed for an additional hour. This solution was then neutralized with NaOH, cooled to room temperature (RT), transferred to 3,500 MWCO cellulose tubing, and dialyzed for 24 h (2×20 L) against distilled water, and lyophilized.

Example 3

DNA Labeling

Covalent labeling of plasmid DNA with fluorophores was performed using tetramethylrhodamine (TMR) LABELIT® reagent (Mirus Bio Corp., Madison, Wis.) according to manufacturer's protocol. Briefly, plasmid DNA and a solution of LABELIT® reagent in methyl sulfoxide (100 mg/ml) were mixed in 1 ml of 10 mM HEPES, pH 7.5 at a LABELIT®/DNA ratio of 5:1 (w/w). The reaction mixture was incubated for 1 h at 37° C. Labeled DNA was then precipitated three times in 70% ethanol with 0.2 M NaCl.

Example 4

DNA Condensation Assay

As DNA is condensed by addition of fcation, there is a measurable reduction in fluorescence as the fluorophores become closer to one another. i.e. fluorescence becomes quenched. The condensation of TMR-labeled DNA was assessed using a quantitative assay based on condensation-induced quenching of a fluorophore covalently attached to DNA. Briefly, TMR-DNA (10 μg) was mixed with various quantities of polyvinyl ethers or melittin in 0.5 ml of 10 mM HEPES, pH 7.5. Rhodamine fluorescence of the samples was measured using a Varian spectrofluorometer (excitation wavelength ($\lambda_{ex}$) of 546 nm; emission wavelength ($\lambda_{em}$) of 576 nm) at RT.

Example 6

Crosslinking with Disulfide-Containing Crosslinking Dialdehyde: Particle Stability and Transfection In Vitro 10 μg/mL of luciferase expression plasmid pCILuc DNA in 500 μl was condensed by the addition of poly-L-lysine (20 μg/mL). To this sample was added 1-12 μg of disulfide dialdehyde prepared according to above procedure. 100 μl of this solution (1 μg of DNA) was added to Hepa-1clc7 cells (mouse hepatoma) which were cultured in 1 mL Dulbecco's modified Eagle's Media containing 10% fetal bovine serum. 10 μg of amphipathic polyvinylether polymer, containing 50/50 molar amounts of butyl and amine groups, were added separately to the cells. After 48 h later, confluency of the cells was estimated. The cells were harvested and assayed for luciferase expression according to standard procedures. The amount of transfection was average transfection for two separate wells of cells.

Polycation-pDNA Stability Assay

Separately, the PLL-condensed, crosslinked particles were assayed for their ability to retain DNA after addition of salt and polyacrylic acid. To determine the stability of crosslinked poly-L-lysine condensed DNA particles. TMR-DNA (10 μg/mL) was condensed at PLL:DNA weight ratio of 2:1 in 5 mM HEPES pH 7.5. After fluorescence of the labeled DNA was measured, sodium chloride and polyacrylic acid were added to 150 mM and 100 μg/mL respectively. Fluorescence of the TMR label was again measured ($\lambda_{ex}$=546 nm $\lambda_{em}$=576 nm). The relative condensation was determined according to formula: percent DNA release=(uncondensed DNA fluorescence−fluorescence after addition of salt/polyanion)/(uncondensed DNA fluorescence−fluorescence of condensed particle)×100.

| disulfide dialdehyde crosslinker (μg) | relative light units | percent DNA release |
|---|---|---|
| 0 | 602,000 | 96% |
| 1 | 711,000 | 68% |
| 2 | 759,000 | 40% |
| 3 | 643,000 | 25% |
| 4 | 2,040,000 | 16% |
| 5 | 1,459,000 | 15% |
| 6 | 957,000 | 14% |
| 7 | 399,000 | 14% |
| 8 | 182,000 | 13% |
| 9 | 127,000 | 12% |
| 10 | 44,000 | 16% |
| 12 | 10,000 | 11% |

Example 7

Polymerization of N-(2-Aminoethyl)-1,3-propanediamine and Dimethyl 5,5'-dithiobis(2-nitrobenzoate) propionimidate-2 HCl on a DNA Template Template polymerization was carried out in 25 mM HEPES buffer, pH 8.0. N-(2-Aminoethyl)-1,3-propanediamine (48 μg, 0.3 mM, Aldrich Chemical Company) was added to a 0.5 mL solution of pCIluc DNA (25 mg, 0.075 mM in phosphate, 2.6 μg/μL pCIluc). Dimethyl 5,5'-dithiobis(2-nitrobenzoate)propionimidate-2 HCl (500 μg, 0.78 mM) was added, and the solution was vortexed. The reaction was incubated at RT for 1 h. A fine yellow precipitate was observed to form during the incubation period. The reaction was centrifuged to remove the precipitate. A portion of the reaction (10 μL) was reduced with 10 mM dithiothreitol (10 μL) to break the disulfide bonds forming the polymer. Portions (0.5 μg) of the intact polymer and the reduced polymer were analyzed on a 1% agarose gel.

Example 8

Formation of DNA/Poly-L-Lysine/Dimethyl 5,5'-Dithiobis(2-nitrobenzoate) propionimidate-2 HCl Complexes pDNA/Poly-L-lysine hydrobromide complexes were prepared by combining plasmid DNA (25 μg) with Poly-L-lysine hydrobromide (95 μg, MW 35 kDa, Aldrich Chemical Company) in 0.5 mL 25 mM Hepes buffer pH 8.0, and the solution was vortexed to mix. The resulting solution was divided into 3 portions. One portion was incubated at RT for 2 h. To the second portion was added dimethyl 5,5'-dithiobis(2-nitrobenzoate)propionimidate-2 HCl (472 mg, 1.5 mmol), the solution was mixed, and incubated at RT for 2 h. To the third sample was added dimethyl 3,3'-dithiobispropionimidate 1.1 mg, 1.5 mmol), the solution was mixed, and incubated at RT for 2 h. After the samples were centrifuged at 12000 rpm for five min.

Ninety degree light scattering measurements were performed (Shimadzo RF-1501 Fluorescence Spectrophotometer). The wavelength setting was 700 nm for both the incident beam and detection of scattering light. The slits for both beams were fixed at 10 nm. The particle size of the resulting complex was determined by light scattering (Brookhaven ZetaPlus Particle Sizer). After determining the initial intensity of scattered light, 15 μL 5 M NaCl solution was added to the complexes while the intensity of scattered light was monitored.

The addition of salt to the non-caged particles led to an immediate increase in the turbidity of the solution indicating aggregation. The non-caged sample also became visibly cloudy. The addition of salt to the particles caged using dimethyl 3,3'-dithiobispropionimidate led to an increase in turbidity of approximately 33%. The addition of salt to the dimethyl 5,5'-dithiobis(2-nitrobenzoate)propionimidate-2 HCl caged complexes lead to no visible rise in turbidity. The particle size of the dimethyl 5,5'-dithiobis(2-nitrobenzoate) propionimidate-2 HCl caged particles was determined (Brookhaven Zeta Plus Particle Sizer) in 150 mM NaCl (physiological concentration). The mean particle diameter was found to be 89.7 nm, 67% of the total number of particles were under 100 nm in size.

The example indicates that dimethyl 5,5'-dithiobis(2-nitrobenzoate)propionimidate-2 HCl caged DNA. The particles formed were stable in physiological salt, and were under 100 nm in size.

Example 9

Demonstration of Reducibility of Disulfide Bond In Vitro pDNA (pCI Luc)/polyethyleneimine (25 kDa, Aldrich Chemical Company)/dimethyl 3,3'-dithiobispropionimidate and pDNA/polyethyleneimine/dimethyl 5,5'-dithiobis(2-nitrobenzoate)propionimidate-2 HCl complexes were prepared in 25 mM HEPES buffer pH 8.0 as described above. All complexes were prepared at pDNA/polyethyleneimine ratios of 1/3. Dimethyl 3,3'-dithiobispropionimidate and dimethyl 5,5'-dithiobis(2-nitrobenzoate) propionimidate-2 HCl were added at the following ratios: 0,3,6,12, and 25. Complexes were incubated 0.5 h at RT, and centrifuged 5 min at 12,000 rpm prior to transfection. Transfections were carried out in 35 mm wells. At the time of transfection, HepG2 monolayers at approximately 50% confluency were washed once with PBS (phosphate buffered saline), and subsequently stored in serum-free media (Opti-MEM, Gibco BRL). The complexes were diluted in Opti-MEM and added by drops, 5.0 μg DNA/ well, to the cells. After a 4 h incubation period at 37° C., the media containing the complexes was aspirated from the cells, and replaced with complete growth media, DMEM with 10% fetal bovine serum (Sigma). After an additional incubation of 42 h, the cells were harvested and the lysate was assayed for luciferase expression (Wolff J A et al. 1990). A Lumat LB 9507 (EG&G Berthold, Bad-Wildbad, Germany) luminometer was used.

pDNA/polyethyleneimine/dimethyl 3,3'-dithiobispropionimidate and pDNA/polyethyleneimine/dimethyl 5,5'-dithiobis(2-nitrobenzoate)propionimidate-2 HCl particles were transfected into Hep G2 cells. pDNA/polyethyleneimine complexes were also transfected as a control. The cell lysates were then analyzed for the expression of luciferase. The results show that while the dimethyl 3,3'-dithiobispropionimidate complexes gave expression results below baseline (<200 RLU), the dimethyl 5,5'-dithiobis(2-nitrobenzoate) propionimidate-2 HCl/pDNA/polyethyleneim ine complexes gave levels of expression that were as high as 120,000 RLU.

The physiologically labile disulfide bonds present in the dimethyl 5,5'-dithiobis(2-nitrobenzoate)propionimidate-2 HCl complexes can be reduced by cultured cells.

Example 10

Template Polymerization (Caging) of Large Polymers

Poly-L-lysine (hydrobromide, molecular mass from 30 to 70 kDa, PLL) and Polyallylamine (hydrochloride, 55 kDa, PAA) were obtained from Aldrich. Histone H1(Type III-S from Calf Thymus) was obtained from Sigma. Dimethyl 3,3'-dithiobispropionimidate (DTBP) was purchased from Pierce. The polycations were dissolved in deionized water: PLL and H1 to concentration 10 mg/ml and PAA to 2 mg/ml. DTBP was dissolved in $H_2O$ (30 mg/ml) immediately before utilization.

DNA/polycation complexes were prepared by the rapid mixing of 37 μg of plasmid DNA with varying amounts of polycations in 750 μl of 25 mM HEPES pH 8.0, 0.5 mM EDTA. The mixtures were kept 30 min at RT and various amounts of DTBP were added. The mixtures were incubated 2 h at RT. 2 M NaCl was added to the complexes to final concentration 100 mM while vigorously mixing.

Ninety degree light scattering measurements were performed using a Fluorescence Spectrophotometer. The wavelength setting was 600 nm for both the incident beam and detection of scattering light. The slits for both beams were fixed at 2 nm. The size of the resulting complexes were determined by light scattering on a Brookhaven ZetaPlus particle sizer. The samples were centrifuged at 12,000 g for 7 min. The amount of DNA remaining in the supernatant was determined by measurement of the absorbency at 260 and 280 nm.

Effect of DNA/PLL ratio and NaCl on the light scattering. PLL was added to plasmid DNA in 0.75 ml of 25 mM HEPES pH 8.0 while vigorously mixing. The kinetics of light scattering was determined immediately after mixing. The turbidity of DNA/PLL complexes was well above that of free DNA at all of PLL concentrations. Complex aggregation increased when the molar charge ratio of PLL to DNA was approximately one and was maximal at ratio 1.17. Further increases in PLL concentration resulted in decreasing of complex turbidity. The light scattering did not change with time for at least for 30 min. At low positive to negative charge ratio, water-soluble nonstochiometrical complexes are formed. At ratio 1 the complexes become insoluble. Increasing the content of polycation may lead to the complex changing its sign and becoming soluble again. With increasing salt concentration to 100 mM the charge stabilized complexes (ratio+/− more then 1) started to aggregate. The rapidity of aggregation decreased with increasing PLL/DNA ratio, but final turbidity level was the same for all samples.

Effect of DTBP on DNA/PLL complexes light scattering. The incubation of DNA/PLL complexes with 0.97 μmol of DTBP for 2 h at RT resulted in a shift of turbidity maximum to a PLL/DNA ratio of 0.88. The addition of NaCl to a concentration of 100 mM did not change light scattering throughout the range of PLL concentration. These results indicate that the addition of DTBP prevented the PLL/DNA complexes from aggregating in 100 mM salt.

The ability to centrifuge the DNA was used as another indication of aggregation (Table 2). All samples were centrifuged 7 min at 12,000 rpm and the amount of DNA in supernatant was determined. As shown, crosslinked PLL/DNA complexes with molar ratio 4.1 and 5.9 did not precipitate. Therefore the size of complexes were very small. In contrast, DNA in noncrosslinked complexes were completely precipitated.

TABLE 2

The effect of DTBP on the precipitation of plasmid DNA/PLL complexes in the presence of 100 mM NaCl.

| PLL/DNA ratio | % DNA in solution after centrifugation | |
|---|---|---|
| | −DTBP | +DTBP |
| 0.585 | 67 | 77 |
| 0.879 | 0 | 0 |
| 1.171 | 0 | 0 |
| 2.342 | 0 | 17 |
| 4.098 | 0 | 97 |
| 5.854 | 0 | 97 |

TABLE 3

The effect of varying the DNA/PLL charge (monomoer:monomer) ratio on the sizes of PLL/DNA complexes with the addition of 0.97 μmol DTBP. The sizes were determined by quasi elastic light scattering and numbers indicate the percent of particles <100 nm or >100 nm. Number in parentheses indicate the size (diameter in nm) of the most abundant species within that size range.

| | Percentage of Particles Less or Greater Than 100 nm | | | |
|---|---|---|---|---|
| | no NaCl | | +100 mM NaCl | |
| DNA/PLL | <100 nm | >100 nm | <100 nm | >100 nm |
| 0.43 | 72(50) | 28(200) | 36(28) | 64(280) |
| 0.65 | 68(42) | 32(196) | 36(63) | 64(304) |
| 0.88 | — | 100(10000) | — | 100(10000) |
| 1.31 | — | 100(10000) | — | 100(10000) |
| 1.74 | 8(65) | 92(150, 680) | 7(84) | 93(1000) |
| 2.61 | 69(33) | 31(118) | 11(91) | 89(836) |
| 4.12 | 96(43.4) | 4(6580) | — | 100(204, 1152) |
| 6.18 | 100(22.4) | — | — | 100(222, 1052) |
| 0.43 + DTBP | 29(55) | 71(331) | 43(31) | 57(131, 374) |
| 0.65 + DTBP | 43(31) | 69(339) | 16(54) | 84(350) |
| 0.88 + DTBP | 13(72) | 87(431, 1640) | 21(41) | 79(707, 4690) |
| 1.31 + DTBP | 87(45, 100) | 3(260) | — | 100(10000) |
| 1.74 + DTBP | 87(45, 99) | 3(256) | 73(55) | 27(191) |
| 2.61 + DTBP | 100(32, 98) | — | 77(51) | 23(130) |
| 4.12 + DTBP | 99(27.9) | 1(6468) | 69(67.6) | 31(142, 2000) |
| 6.18 + DTBP | 94(35.2) | 6(6580) | 96(68) | 4(6813) |
| 4.12 + DTBP + DTT | | | — | 100(362, 8800) |
| 6.18 + DTBP + DTT | | | — | 100(381, 8755) |

In Table 3, it is clear that PLL/DNA complexes with ratio higher than 1.3 became substantially less prone to aggregation in the presence of 100 mM NaCl after DTBP crosslinking. The PLL/DNA complex stabilized reaction was intra complex crosslinking because the treatment of the modified PLL/DNA complexes with ratio 4.12 and 6.18 by 50 mM DTT for 1 h resulted in aggregation. In this condition the crosslinking should be cleaved without changing the level of lysine modification.

Effect of PLL/DTBP ratio on the size and stability of PLL/DNA complexes. The PLL/DNA complex in ratio 4.12 was treated by different concentrations of DTBP during 2 h. The size of particles without and in presence of 100 mM NaCl was determined by quasi elastic light scattering.

TABLE 4

The effect of varying the DTBP/PLL ratio (molar ratio of DTBP to lysine residue) on the sizes of PLL/DNA complexes. The sizes were determined by quasi elastic light scattering and numbers indicate the percent of particles <100 nm or >100 nm. Number in parentheses indicate the size (diameter in nm) of the most abundant species within that size range.

| | Percentage of Particles Less or Greater Than 100 nm | | | |
|---|---|---|---|---|
| DTBP/PLL Ratio | no NaCl | | +100 mM NaCl for 1 h | |
| | <100 nm | >100 nm | <100 nm | >100 nm |
| 0 | 75(88) | 25(586) | — | 100(7524) |
| 1.01 | 93(44) | 7(6874) | 37(92) | 63(600) |

TABLE 4-continued

The effect of varying the DTBP/PLL ratio (molar ratio of DTBP to lysine residue) on the sizes of PLL/DNA complexes. The sizes were determined by quasi elastic light scattering and numbers indicate the percent of particles <100 nm or >100 nm. Number in parentheses indicate the size (diameter in nm) of the most abundant species within that size range.

| DTBP/PLL | Percentage of Particles Less or Greater Than 100 nm | | | |
|---|---|---|---|---|
|  | no NaCl | | +100 mM NaCl for 1 h | |
| Ratio | <100 nm | >100 nm | <100 nm | >100 nm |
| 2.03 | 95(35) | 5(550) | 75(66) | 25(190, 4658) |
| 3.05 | 100(52) | — | 100(86) | — |

Table 4 shows that an excess of DTBP was needed for complex protection from salt dependent aggregation. It should be noted that DTBP up to ratio of 3.05 did not induce crosslinking between DNA/PLL particles. For samples with DTBP/PLL ratio 2.03 and 3.05 zeta potential were 16.16±3.23 mV and 20.33±3.3 mV respectively in 25 mM HEPES pH 8.0, 100 mM NaCl.

Stability of DNA/PLL complexes to disruption by polyanion dextran sulfate (DS). DNA/PLL complexes (molar ratio of 0.87, 1.74, 3.04 or 4.35) were prepared as before but in 1 ml of buffer. 0.97 μmol of DTBP were added. The mixtures were incubated 2 h at RT. 10 μl of ethidum bromide (EB) (0.1 mg/ml) were added in every sample and the samples were incubated 30 min. The aliquot portions of DS were then added sequentially, with mixing. After each addition, the fluorescence was allowed to stabilize 30 seconds.

Addition of PLL to DNA in solution gave rapid falls in fluorescence, corresponding to complex formation (condensation of DNA). Addition of DS to pre-formed complexes can restore EB fluorescence and can be taken as indicator of complex stability. Without DTBP, the EB fluorescence rose with the addition of DS in every ratio of PLL/DNA. With DTBP, the increase was attenuated and there was a clear influence of DTBP modification on complex stability: the fraction of complexes could not be disrupted in any DS concentration. The part of complexes which are stable to disruption by DS depended on PLL/DNA ratio.

DNA/PAA complexes. Polyallylamine (PAA) is similar to PLL and contains primary amino groups. But average pK of PAA is lower than PLL because of the stronger influence of one group to another.

The effect of varying the DNA/PAA ratio on the sizes of PAA/DNA complexes with or without the addition of DTBP. The sizes were determined by quasi elastic light scattering and numbers indicate the percent of particles <100 nm or >100 nm. Number in parentheses indicate the size (diameter in nm) of the most abundant species within that size range.

| PAA/DNA Ratio | Percentage of Particles Less or Greater Than 100 nm | | | |
|---|---|---|---|---|
|  | no NaCl | | +NaCl | |
|  | <100 nm | >100 nm | <100 nm | >100 nm |
| 2.17 + DTBP | 7(106) | 77(455), 16(4436) | — | 100(2064) |
| 4.34 + DTBP | 93(66) | 7(6900) | 70(94) | 30(916) |
| 6.51 + DTBP | 93(53) | 6(163) | 81(92) | 19(870) |
| 8.68 + DTBP | 97(55) | 3(5607) | 81(62) | 19(182) |
| 4.34 | 55(71) | 45(352) | .4(79) | 96(863) |

The results in Table 5 were very similar to the results with PLL/DNA complexes, but large excess of polycations were required for the preparation of stable small particles.

DNA/Histone H1 complexes. H1 has total positive charge of 55 per molecule (MW 21.3 kDa) and can form an inter polyelectrolyte complex with DNA. In contrast to PLL and PAA, interaction of H1 with DNA led to considerable increase of turbidity in a broad range of H1 concentration. The turbidity was not changed after addition of 100 mM NaCl. Treatment of H1/DNA complex with charge ratio 3.42 by DTBP led to significant decrease of turbidity from 1929 to 348. Addition of NaCl caused the turbidity to increase to 458. The centrifugation of H1/DNA complexes in buffer with 100 mM NaCl 7 min at 12,000 rpm resulted in precipitation of DNA. After DTBP modification, most part of DNA stayed in solution, indicating presence of small particles. Table 6 shows that the sizes of the particles formed with DTBP (Table 6B) in 100 mM NaCl were much smaller that the particles formed without DTBP (Table 6A).

TABLE 6

The effect of varying the H1:DNA charge ratio on the sizes of H1/DNA complexes without (A) or with (B) the addition of DTBP. The sizes were determined by quasi elastic light scattering and numbers indicate the percent of particles <100 nm or >100 nm. Number in parentheses indicate the size (diameter in nm) of the most abundant species within that size range.

| Charge ratio | Percentage of Particles Less or Greater Than 100 nm | | | |
|---|---|---|---|---|
|  | −NaCl | | +NaCl | |
| (+/−) | <150 nm | >150 nm | <150 nm | >150 nm |
| A. H1/DNA-no DTBP | | | | |
| 1.55 | 7(44) | 29(377), 64(1376) | 47(25) | 36(491) |
| 3.1 | 6(75) | 88(500), 10(6000) | — | 92(470), 8(8000) |
| 6.2 | — | 10(159), 90(589) | — | 62(350), 38(1825) |
| 9.3 | 9(113) | 91(348) | — | 2(208), 98(1404) |
| B. H1/DNA + DTBP | | | | |
| 1.55 | 19(27), 6(131) | 75(886) | — | 84(892), 16(8000) |
| 3.1 | 28(37) | 12(168), 60(603) | — | 28(171), 72(512) |
| 6.2 | — | 75(166), 25(1168) | 47(55) | 53(222) |
| 9.3 | 48(117) | 52(306) | 56(75) | 44(172) |

DNA template polymerization of large polymers yielded small particles that did not aggregate in physiological salt solutions. The ability to prepare small particles of condensed DNA that do not aggregate in a physiologic salt solution will be an extremely useful formulation for gene transfer and therapy.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A method for delivering a polyion to a cell, comprising:
   a) noncovalently associating molecules with the polyion in a solution outside a cell;

b) adding a crosslinker wherein said crosslinker contains a disulfide bond and forms covalent linkages between moieties of the molecules in the presence of the polyion, thereby forming a complex; and, c) delivering the complex to the cell.

2. The method of claim 1 wherein the molecules are selected from the group consisting of polycations and polyanions.

3. The method of claim 2 further comprising attaching functional groups to the molecules.

4. The method of claim 3 wherein the functional groups consist of targeting groups.

5. The method of claim 4 wherein the targeting groups are selected from the group consisting of nuclear localizing signals, ligands that bind to cellular receptors, and releasing signals.

6. The method of claim 3 wherein the functional groups consist of interaction modifiers.

7. The method of claim 3 wherein attaching functional groups to the polymers changes the net charge of the complex.

8. The method of claim 1 wherein the polyion comprises a polyanion.

9. The method of claim 8 wherein the polyanion comprises nucleic acid.

10. The method of 9 wherein the molecules consists of polycations.

11. The method of claim 9 wherein the polycation consists of a polyamine.

12. The method of claim 11 wherein associating molecules with the nucleic acid condenses the nucleic acid.

13. The method of claim 11 wherein the polyamine is selected from the list consisting of: polylysine, polyethyleneimine, polyallylamine, and histone.

14. The method of claim 9 wherein associating molecules with the nucleic acid comprises:

a) condensing the nucleic acid with polycations to form a positively charge binary complex; and, b) associating polyanions with the binary complex to form a ternary complex that is less positively charged than the binary complex.

15. The method of claim 1 wherein the disulfide bond consists of an activated disulfide bond.

16. The method of claim 15 wherein the activated disulfide bond is cleaved more rapidly than oxidized glutathione when measured under the same conditions.

17. The method of claim 15 wherein the activated disulfide bond is constructed from thiols in which at least one of the constituent thiols has a lower thiol pKa than glutathione thiol pKa when measured under the same conditions.

* * * * *